United States Patent [19]

Gutierrez et al.

[11] Patent Number: 4,530,995

[45] Date of Patent: Jul. 23, 1985

[54] METHODS FOR STORAGE OF GUAYULE PLANT MATERIAL

[75] Inventors: Richard Gutierrez, Canal Fulton; Edward L. Kay; David J. Serbin, both of Akron, all of Ohio

[73] Assignee: The Firestone Tire & Rubber Company, Akron, Ohio

[21] Appl. No.: 509,481

[22] Filed: Jun. 30, 1983

Related U.S. Application Data

[62] Division of Ser. No. 307,405, Oct. 1, 1981, Pat. No. 4,405,532.

[51] Int. Cl.³ .................................................. C08C 2/00
[52] U.S. Cl. ...................................... 528/930; 524/255
[58] Field of Search ...................... 260/814, 816, 818; 524/254, 255; 528/930, 935

[56] References Cited

U.S. PATENT DOCUMENTS

| | | | |
|---|---|---|---|
| 2,390,860 | 12/1945 | Williams | 260/818 |
| 2,434,412 | 1/1948 | Jones | 260/816 |
| 2,459,369 | 1/1949 | Tint | 260/818 |

*Primary Examiner*—Christopher A. Henderson
*Attorney, Agent, or Firm*—Daniel N Hall

[57] ABSTRACT

A method of storing guayule and guayule-like plant material prior to processing which comprises mixing the material in communited form with at least one essentially water-free organic liquid to form a slurry in which the material is protected from contact with oxygen and storing said slurry for at least about 24 hours is disclosed. Preferably, the organic liquid is an alcohol, ether, ester, ketone, or hydrocarbon and optionally the slurry also contains an oxidation stabilizer.

4 Claims, No Drawings

METHODS FOR STORAGE OF GUAYULE PLANT MATERIAL

CROSS-REFERENCE TO RELATED APPLICATIONS

This application is a division of copending U.S. Ser. No. 307,405 filed Oct. 1, 1981 now U.S. Pat. No. 4,405,532.

BACKGROUND OF THE INVENTION

1. Field of the Invention:

This invention relates to methods for storage of material from guayule and guayule-like-plants prior to its processing to recover valuable components such as rubber, resin, bagasse, etc. Specifically, it relates to mixing the material in communited form with organic liquid to form a slurry and storing the slurry for at least 24 hours. It also relates to the slurry thus formed.

2. General Background:

A practical convenient and effective method and system for the storage of guayule shrub prior to processing is needed. It is clear, for example, a commercial unit designed to recover valuable guayule rubber, resin and other products will be operated most efficiently on a continuous basis; intermittent production is costly in terms of operating expenses as well as lost production. Productivity decreases and energy costs increase if interruptions in supply of raw material cause shut downs of a processing unit.

Disruption of raw material supply might well be caused by weather conditions which prevent harvesting for short or prolonged periods. Thus, it is obvious that an adequate continuous supply of guayule raw material would increase the effciency of a processing unit.

It is also well known that space requirements for raw material storage can significantly add to costs. Although storage of whole guayule shrub might be preferred because of the relatively low surface area of the shrub exposed to the atmosphere, economics are improved if the shrub is communited (ground) thus requiring less storage space than the bulky harvested shrub. In addition, the use of unground pollarded guayule raw material interferes with transfers. The bulk handling of essentially free flowing, ground guayule shrub is greatly preferred over the handling of low density, bulky, unground, whole or pollarded guayule shrub.

Heretofore, the temporary storage of ground guayule shrub has been considered technically feasible; however, storage time has been severely limited. The storage time could be increased by storing the ground material under an inert gas; but again this is an expensive operation and, from a technical standpoint, the displacement of all oxygen from the stored shrub is very difficult, if not impossible.

In addition to the above problems of using inert gas, a very practical problem of compaction of the ground shrub by the very weight of the shrub itself is encountered. Furthermore, during the grinding of the guayule shrub, resins are released which tend to bind the ground shrub particles into agglomerates. If even a small amount of moisture is present in the shrub, simple sugars present in the shrub can also aggravate this agglomeration problem.

BRIEF DESCRIPTION OF THE INVENTION

The present invention is directed to a practical, efficient method and system of storing guayule and guayule-like plant material prior to processing which comprises mixing the material in communited form with at least one essentially water-free organic liquid to form a slurry in which the material is protected from contact with oxygen and storing said slurry for at least about 24 hours. Usually the organic liquid is selected from (1) alcohols, ethers, esters and ketones having one to eight carbon atoms, (2) hydrocarbon solvents having a boiling range within about 20°–100° C., (3) concentrated resin micella (as defined below), (4) hydrocarbon/guayule rubber/guayule resin micella (as defined below) (5) hydrocarbon/guayule rubber micella comprising said hydrocarbon solvent and about 2–4% guayule rubber, and (6) mixtures thereof.

Typically, the liquid is acetone or acetone/resin micella and contains a stabilizer such as a para-phenylenediamine stabilizer. Usually the plant material is of the entire non-defoliated plant and is dried to a moisture content of about 5–25% before forming the slurry. In some embodiments, the slurry is subjected to mild agitation. The slurry formed by the inventive method is another aspect of the invention.

An advantage of the present invention is that storage of ground guayule under an organic solvent effectively prevents development of offensive odors, presumably due to the degradation of the guayule shrub, as well as microfloral growth on the shrub. In addition, the invention permits partial or essentially complete extraction of useful products from the shrub during storage, thus reducing costs, time and equipment required for the extraction of useful products from freshly harvested guayule. Another advantage of the invention is that the communited guayule/organic solvent slurry can be pumped from one process unit to another thus avoiding undue exposure of material to air.

DETAILED DESCRIPTION OF THE INVENTION

The guayule and guayule-like plant material which can be advantageously used in this invention includes a large number of plant species bearing rubber and rubber-like hydrocarbons. Particularly useful is guayule itself (*Parthenium argentatum*), as well as Rabbit-Brush (*Crysothamnus nauseousus*), Rubbervine (*Cryptostegia grandiflora*), Milkweeds (*Asclepias incarnata, sublata, syriaca,* et al.), Goldenrods (*Solidago altissima, graminifolia, leavenworthii, rigida,* et al.), Sow thistles (*Sonchus arvensis oleraceous,* et al.), Rosin Weeks (*Silphium species*), Mountain Mints (*Pycnanthemum species*), and *Cacalia atriplicifolia*. Many other plants which produce rubber and rubber-like hydrocarbons are known, particularly among the compositae, Euphorbiaceae, Labiatae, and Moraceae and the invention is applicable to these species also. Current efforts by plant breeders to develop varieties high in hydrocarbon and rubber content of these and other species will also provide plant material suitable for use in the invention.

This plant material can be the entire, whole bush or shrub or it can be defoliated material. By "whole" or "entire" guayule shrub is meant the complete shrub including the roots, base, stem, branches and leaves. "Pollarded" guayule shrub is included in the above definition of whole, entire guayule shrub. "Pollarded" shrub is shrub which is harvested by cutting the shrub a few centimeters above ground level and harvesting the greater portion of the base, branches, stems and leaves. The root system is left in the soil to generate another plant. By defoliated guayule shrub is meant the whole guayule shrub (including pollarded shrub) which has been treated to remove essentially all of the leaves.

Wild natural guayule shrub is currently available in Texas, and this source provides the raw material for the experiments described in the examples set forth below. These examples would give essentially the same results with cultivated guayule and guayule-like plants of all varieties and of generally higher rubber contents.

The storage method of this invention comprises mixing the aforedescribed plant material in communited (i.e., ground) form. The material can be communited by any one or more of a variety of known mechanical techniques. Usually a mill such as a hammermill, roll mill, stove mill, ball mill or pulp mill is used. A hammermill with an air conveyor is convenient.

The comminunited material is mixed with at least one essentially water-free organic liquid. This liquid contains less than about 1% water and is typically (1) alcohol, ether, ester or ketone having one to eight carbon atoms such as methanol, ethanol, octanol (all isomers), di-ethyl or di- (n-propyl) ether, ethyl acetate, n-propyl propionate, methyl ethyl ketone, 2-heptanone and the like; (2) hydrocarbon solvent having a boiling range within about 20°-100° C., (3) concentrated resin micella comprising said ethers, esters and ketones and at least about 4% guayule resin, (4) hydrocarbon/guayule rubber/guayule resin micella comprising said hydrocarbon solvent and at least about 4% combined guayule resin and rubber, (5) hydrocarbon/guayule rubber micella comprising said hydrocarbon solvent and about 2-4% guayule rubber, and (6) mixtures of (1)+(5).

The term "resin miscella" is derived from the miscella used in the soybean industry to describe a solvent extract of the soybean; in the present case, the resin, rubber or rubber/resin is the extract. Thus, an acetone/resin miscella of at least about 4%, such as preferred as an oxygenated organic solvent in the present invention, is an acetone extract containing at least about 4% guayule resin. Similarly, a hydrocarbon solvent/guayule resin/guayule rubber miscella of at least about 4% comprises hydrocarbon solvent and at least 4% combined resin and rubber. The miscella used in the present invention often contain up to about 40% resin and exhibits unusual solvent properties with respect to extracting resin. Thus, typical miscella for use in the present invention comprises an essentially anhydrous organic liquid and about 4-40% total resin, and optionally, lower amounts (e.g., 2-4%) rubber.

Acetone is generally preferred as the organic liquid, but other oxygenated organic liquids that can be utilized in lieu thereof include the lower molecular weight alcohols such as methanol, ethanol, n-propanol, isopropanol, n-butanol, 2-isobutanol, the pentanols, hexanols, heptanols and octanols; anhydrous ketones such as 2-butanone, 3-methyl-2-butanone, 2-pentanone, 3-pentanone, the hexanones, heptanones and octanones. Analogous low molecular weight ethers and esters are also effective.

Although commercial grade hexane, which is a mixture of isomers, is the preferred hydrocarbon solvent (2), other such solvents that can be utilized in place of hexane include liquified propane, butanes, pentanes, heptanes, octanes and nonanes and mixtures thereof. Alicyclics such as cyclopentane, cyclohexane and cycloheptane can also be used as can be aromatics such as benzene, toluene and the xylenes. Optimization can be achieved with a minimum of routine experimentation.

As noted above mixtures of two or more of (1), (2), (3), (4) and (5), either within or between classes, can be used in the invention.

The aforedescribed communited material and liquid are mixed by standard techniques to form a slurry; that is, a more or less free-flowing homogenous mixture of liquid and finely divided solid. Optionally, this slurry can be subjected to mild agitation, continually or intermittently. Such agitation can be effected by any convenient means such as paddles, pumps, propellers, bubbling with inert gas, etc.

The slurry can also optionally contain at least one stabilizer against oxidation of guayule resin and/or rubber. Such stabilizers are soluble in the organic liquid; that is, they dissolve in the liquid at least to the extent of 0.01 gm in 100 cc of liquid at 20°. Many stabilizers against oxidation of resin and/or rubber are known; see, for example, the article in Kirk-Othmer "Encyclopedia of Chemical Technology," Second Edition, Vol. 17, John Wiley and Sons, New York (1968), pp. 509–542 entitled "Rubber Chemicals" as well as Kirk-Othmer, ibid, Third Edition, Vol. 2, pp. 329 et seq. entitled "Diaryl Amines." These materials are called stabilizers; usually when they protect an oxygen-susceptible material during isolation; anti-oxidants then protect the material during processing and use. A stabilizer added before or during isolation often remains in the isolated material where it functions successful as an antioxidant.

Suitable stabilizers for use in the present invention include the symmetrical and unsymmetrical para phenylenediamines which can be represented by the general formula:

$$R'R\,N-Ph-N\,RR'$$

wherein Ph is a phenylene group, each R is independently hydrogen or a hydrocarbuyl group, and each R' is independently a hydrocarbyl group. Each R and R' can be alkyl or aryl, such as butyl, pentyl, hexyl, heptyl, octyl and the like (all isomers) and phenyl, tolyl, xylyl, naphthyl and the like (all isomers). Typical paraphenylenediamines used in the present invention include:

N,N'-bis(phenyl)-p-phenylenediamine
N,N'-bis-B-(naphthyl)-p-phenylenediamine
N,N'-bis-(alkyl phenyl)-p-phenylenediamine N-alkyl, N'-phenyl-p-phenylenediamine
N,N'-bis-(pentyl)-p-phenylenediamine Other classes of stabilizers such as phenols, hindered alkyl phenols, phosphites, (aryl and alkyl), dithiophosphates (aryl and alkyl) and the like are also effective.

The slurry of communited plant material and organic liquid is such that the material is protected from contact with oxygen, particularly air. Usually this is accomplished by confining the slurry to an essentially closed container and/or using enough liquid so that the bulk of the material is under the liquid surface. Vigorous measures to exclude oxygen are not generally necessary. Usually it is sufficient that measures be taken to avoid the unnecessary introduction of oxygen, particularly in the form of air. Such measures include using essentially closed containers, avoiding subsurface introduction of oxygen or air and the like. Often the organic liquid, being relatively volatile, provides a vapor blanket over the slurry surface that adequately protects the material from contact with oxygen.

The slurry of the invention is stored for at least about 24 hours. Longer storage periods of hours, days, weeks and months can be used as required for convenience of further processing. Generally, however, storage does not exceed 12 months. Storage temperatures are not critical and are usually ambient. Care should be taken, however, to avoid excessive evaporation of liquid.

An inherent advantage of the present invention is that a partial or whole extraction of valuable products can be realized during storage of communited guayule plant material. In addition, by following the procedures disclosed herein, it is possible to increase the concentration of valuable extracts (e.g., resin and rubber) of guayule shrub in the organic storage liquid. An increase in the concentration of extracts of guayule shrub in the liquid has significant practical implications. The amount of energy required to recover the extracts via removal of the liquid usually by distillation per unit weight of extract is significantly reduced as the concentration of extract is increased. In general, extraction of ground guayule shrub whether by immersion or percolation is conducted under "flooded" conditions. By "flooded" conditions is meant that the ground guayule shrub is completely covered with the extracting solvent resulting in a more rapid extraction. To attain the flooded condition a minimum volume of solvent must be used to cover the ground shrub. This minimum volume of extracting solvent essentially dictates the upper limit of concentration of extracts that can be attained from a given volume of ground plant material. It should also be noted that if the concentration of valuable extracts in the plant material is low, the concentration of extracts in the extracting liquid will be low because a definite minimum volume of extracting solvent is required to flood the material. If the concentration of valuable extracts in the shrub is relatively high, the concentration of extract in the extracting solvent will be relatively high assuming that the same solvent volume/shrub remains constant.

To increase the concentration of extract in the extracting solvent it is possible that, after at least 24 hours of storage, the extract/liquid could be drained from the stored plant material and utilized as a liquid for additional ground shrub. The partially or wholly extracted plant material could be processed to further extract all of the value from the shrub or, in the case of wholly extracted material, "flushed" with extracting solvent in a countercurrent manner to remove occluded extract/solvent from the shrub. This extract/liquid flush could be used as a storage liquid for fresh plant material and the process repeated until a desired practical concentration of extracts is achieved. Then, the solvent could be removed from the resin/rubber extract resulting in a significant energy savings which is reflected in a significantly lower processing cost.

An alternative procedure is to store ground guayule plant material under the liquids herein disclosed or containing guayule resin and/or rubber obtained by the foregoing procedure and allow the plant material/liquid/extract suspension to sit for a sufficient time to permit settling out of plant material fines. Then the clarified supernatant micella can be drawn off and processed to recover the extract. This alternative procedure has the added benefit of producing a clarified liquid solution which can be processed directly to recover the extract or receive a minimum amount of processing to remove debris via filtration or centrifugation. Essentially, the alternative procedure consists of three concurrent or simultaneous required processing steps; storage, extraction and clarification.

Another alternative procedure is to store deresinated guayule shrub under a hydrocarbon solvent. Depending upon commercial plant production schedules, it may be advantageous to process ground guayule shrub to extract resin from the shrub. The deresinated plant material could then be stored under hydrocarbon solvent, as herein defined, to effect simultaneous protective storage of the material and partial or complete extraction of guayule rubber.

In the following representative examples, which exemplify the invention, acetone and commercial hexane are used as organic liquids. In these examples, as elsewhere in this specification and the appended claims, the parts and percentages are by weight and temperatures are by degrees centigrade, unless specifically indicated otherwise.

EXAMPLE 1

Comparison of Varying Storage Conditions According to the Invention and Otherwise To demonstrate the beneficial effects of the invention, freshly ground guayule shrub was stored in air as well as under inert gases and under various liquids. Water was used in one experiment and aqueous ammonia and aqueous sodium bisulfite in others. Ammonia and sodium bisulfite are generally known and used for improving the storage stability of natural products. Ground guayule shrub was also stored according to the invention using acetone and hexane as the organic liquid.

These samples were periodically observed and the development of offensive odors and microfloral growth noted. Because the odor of a substance is very subjective and difficult to quantify, a numerical rating as shown in Table I was used to describe odor development. Microfloral growth ratings were based on visual inspection of the storage samples. Although microfloral growth per se may not be deleterious to effective storage, the microfloral growth observed was usually associated with an offensive odor.

Referring to Table I, it will be noted that some offensive odor and microfloral growth was observed after one week in all the samples except those stored under acetone and hexane according to the invention; the offensive odor and microfloral growth progressively increased throughout the three-month period of the storage test in the comparative systems, such as water, as set forth in Table I. No odor, however, other than the solvent odor, was noted in the ground guayule shrub stored under acetone and hexane. No microfloral growth was noted in these samples even after three months' storage; in contrast nauseating odor and heavy microforal growth were observed in samples stored using inert gas or even the specified inhibited aqueous solutions.

EXAMPLE 2

Shrub Volume Change During Storage

As briefly discussed previously, storage of ground guayule shrub in water on a temporary basis may be technically feasible. Experience shows, however, that storage of ground guayule shrub in water is somewhat difficult because depending upon the volume ratio of water to shrub, some of the shrub floats and comes in contact with air. If the amount of water used is just sufficient to cover the shrub, within approximately a day the shrub actually expands presumably by imbibing water. This results in overflow of the shrub from the storage container. Since this expansion of shrub under water could pose some very practical problems, experiments were designed to demonstrate the apparent change in volume of shrub stored using water, acetone and hexane. The experimental technique consisted of charging a known amount of ground shrub to a graduated glass vessel, adding the solvent, mixing the contents and then allowing the samples to stand. Periodic observations made on the samples are summarized in Table II.

Referring to the data presented in Table II, it will be noted that the bulk of the shrub stored under water floated near the surface after one day and then gradually sank (waterlogged) after about one week. In contrast, shrub stored under acetone and hexane immediately sank to the bottom of the vessel thereby ensuring immediate protection by a liquid barrier against oxygen contact.

It should also be noted that the apparent volume of shrub stored under acetone and hexane slightly decreased during storage. This is believed to be due to the extraction of resin and rubber and the resulting decrease in apparent volume of the shrub. Actually the accuracy of the volume change observations does not allow quantitative estimates of the amount of product extracted but the experiments do indicate that some resin and/or rubber is extracted. In addition, it was noted that storage of shrub under acetone rapidly resulted in the development of a greenish color in the supernatant acetone; the color of the supernatant hexane was more of an olive amber. The decrease in total volume of the sample is attributed to evaporation of solvent.

It was also observed that no offensive odors or microfloral growth developed in the samples of shrub stored under acetone or hexane even after 2.5 months. In contrast, the shrub sample stored under water had an offensive putrid odor.

EXAMPLE 3

Molecular Weight of Recovered Rubber

Examples 1 and 2 show that storage of ground guayule shrub with organic liquids, according to the invention, is a practical, effective storage procedure. This example demonstrates that stabilizers which are soluble in organic liquids can be used in the invention to further improve the storage stability of guayule shrub and, specifically, the guayule rubber contained in the shrub.

The experimental procedure was to place 2.000 Kg of ground guayule shrub under acetone or hexane. To one of each of the samples stored under acetone or hexane was added 0.25 gram of a commercial para-phenylenediamine stabilizer. No stabilizer was added to the other samples. All the samples were stored a total of 27 days and then inspected for development of offensive odor and micorfloral growth. As recorded in Table III, no odor other than the odor of solvent was noted and no microfloral growth was observed at the end of the test period.

The rubber contained in the acetone samples was recovered by separating the plant material by filtration and extracting the recovered material with hexane. The hexane was evaporated to yield the rubber. Resinous rubber was recovered from the shrub stored under hexane by simply filtering the slurry to recover a hexane solution of resinous rubber and evaporating the hexane. The resinous rubber was then extracted with acetone to remove most of the resin. A small amount of para-phenylenediamine stabilizer was added to each rubber sample at this stage to prevent degradation of rubber molecular weight during handling and testing in a gel permeation chromatograph (gpc) to determine weight average molecular weight (Mw) and number average molecular weight (Mn) of the recovered rubber samples. Molecular weight data on the recovered rubber samples are also presented in Table III. For comparative purposes, gpc molecular weight data on rubber recovered from freshly ground shrub by a water flotation process are also shown in Table III.

Referring to Table III, it should be noted that rubber recovered from the samples stored under hexane have molecular weights essentially equivalent to the values observed on the guayule rubber recovered directly from freshly ground shrub (i.e., shrub that has not been stored after grinding). The experimental Mw and Mn values on the rubber recovered from shrub stored under hexane actually are numerically slightly higher than the respective values obtained on the rubber recovered directly from fresh shrubs. This result is probably within experimental variations occuring in recovering the rubber and doing the gpc analyses. Considering the relatively involved experimental procedures utilized, the data are essentially equivalent.

Referring to the molecular weight data concerning the guayule rubber recovered from shrub stored under acetone, it will be noted that both the Mw and Mn values are lower than the values on the rubber recovered from shrub stored under hexane as well as from the freshly ground shrub. The lowest molecular weights were obtained on rubber recovered from shrub stored under acetone without inhibitor. Although the molecular weights of the rubber recovered from shrub stored under acetone were somewhat lower than the other values, the rubber recovered is considered useful and of definite economic value. It should be noted that the experimental procedure used did not involve purging the storage vessel with inert gas prior to charging shrub/solvent. On a large commercial scale, purging of vessels with inert gas prior to charging organic solvents is a common practice; thus a more effective storage of guayule shrub under organic solvents is expected under large scale operation. Although the invention is not limited by theory, the lower molecular weight rubber recovered from shrub stored under acetone may be due to the presence of dissolved oxygen in the acetone. The amount of dissolved oxygen in acetone used in a commercial operation should be significantly less than that present in the small scale experiment described herein.

As a final comment on the molecular weight data recorded in Table III, it should be noted that in a process for extracting rubber from shrub, the quality of rubber extracted reflects the quality of rubber originally present in the shrub. Variations in molecular weight are to be expected with variations of guayule shrub.

EXAMPLE 4

Rate of Product Extraction During Storage

One of the benefits of the inventions is that some or all of the desired guayule products can be extracted during storage. To demonstrate this aspect of the invention, ground guayule shrub was stored with acetone and with hexane and the rate of extraction of resin and resin/rubber, respectively, monitored over 43 days.

To do this, a small sample of the supernatant liquid was removed periodically from the stored sample and the amount of product in the sample determined by evaporation of solvent. Particular care was taken to allow all extraneous material (specifically shrub fines) to settle from the liquid sample taken so that only solvent and desired product (resin and resin/rubber) were measured. In addition, the ratio of solvent/shrub was kept high so that the effect of solvent absorbed in the shrub (which presumably does not contain solute) on the calculation of theoretical concentration based on analyses of the shrub would be minimal.

Calculated product extraction efficiencies as a function of storage time are summarized in Table IV.

Referring to the data in Table IV, it will be noted that extraction efficiency of guayule resin from shrub stored under acetone is relatively high even after one day (80%) and is essentially complete after about 10 days (96%). In contrast, extraction of resin/rubber by hexane after one day is 73% and increases slightly during the remaining storage time. The lower extraction efficiency observed with the resin/rubber/hexane system may be the result of incomplete rupture of the cells containing rubber thus requiring hexane to diffuse first into the cell then and diffuse out of the cell as a hexane/rubber solution. Alternatively, the highly polar portion of the guayule resin is not very soluble in hexane. Additional experimental data on this phenomenon is presented in Example 5.

In any event, the product extraction data presented in Table IV demonstrate a useful aspect of the invention.

The molecular weight data obtained on the rubber recovered from the shrub stored for 43 days shows that the rubber would be of economic value. As with other samples, no offensive odors or microfloral growth were observed after 43 days storage.

EXAMPLE 5

The Effects of Agitation and Shrub Particle Size on Product Extraction Efficiencies During Storage of Guayule Shrub Under Solvent In Table V data developed in example 5 are summarized.

Essentially the same experimental procedure was used except the samples were mildly agitated by gentle rotation of the sample vessel. To obtain an insight into the effect of shrub particle size on product extraction efficiencies, a sample of shrub was "flaked" to ensure that essentially all of the cells containing rubber were ruptured to obviate any solvent diffusion effects into and out of the cells to extract rubber.

Referring to the data summarized in Table V, it should be noted that gentle agitation significantly improves the rate of extraction of products in all the samples. The flaking operation also significantly aids the extraction efficiency of products.

It should be noted that the greater than theory yield reported on the extraction efficiency of resin with acetone obviously represents experimental error or the presence of sufficient moisture in the shrub to effect a partial extraction of some water-soluble material into the acetone.

It should be also stated that shrub stored under acetone rapidly settles and even concentrated resin/acetone solutions are of low viscosity. In contrast, shrub stored under hexane settles less rapidly because the hexane/resin/rubber micella is relatively viscous. Since a polar solvent (acetone) and a nonpolar solvent (hexane) were demonstrated to be effective in the invention, various combinations of nonpolar and polar solvents should also be effective.

While the invention has been described and exemplified herein by reference to various specific materials, procedures and examples, it is to be understood that it is not to be restricted in any way to these. Numerous variations of such details can be used and are within the scope of the invention, as will be appreciated by those skilled in the art.

TABLE I

Observations on Development of Offensive Odor and Microfloral Growth on Samples of Ground Guayule Shrub Stored Under Various Conditions Ambient Temperature (25° C.) Storage, After

| | 1 Day | | 1 Week | | 1 Month | | 3 Months | |
|---|---|---|---|---|---|---|---|---|
| | Odor | M/F* Growth | Odor | M/F* Growth | Odor | M/F* Growth | Odor | M/F* Growth |
| Ground Shrub Stored In | | | | | | | | |
| Air | 0 | 0 | 1 | 1 | 3 | 3 | 3 | 3 |
| Nitrogen | 0 | 0 | 1 | 1 | 2 | 2 | 3 | 3 |
| Carbon Dioxide | 0 | 0 | 1 | 1 | 2 | 2 | 3 | 3 |
| Water | 0 | 0 | 1 | 1 | 2 | 3 | 3 | 3 |
| Aqueous | | | | | | | | |
| Ammonia | 0 | 0 | 1 | 1 | 2 | 3 | 3 | 3 |
| Sodium | | | | | | | | |
| Acid | | | | | | | | |
| Sulfite | 0 | 0 | 1 | 1 | 2 | 3 | 3 | 3 |
| Under | | | | | | | | |
| Acetone | 0 | 0 | 0 | 0 | 0 | 0 | 0 | 0 |
| Hexane | 0 | 0 | 0 | 0 | 0 | 0 | 0 | 0 |

Significance of Numerical Ratings:
Odor
0 - Original odor
1 - Somewhat objectionable
2 - Very objectionable
3 - Nauseating
M/F* = Microfloral Microfloral Growth
0 - None
1 - Trace growth on surface
2 - Moderate growth on surface
3 - Heavy growth; appears under surface

TABLE II

Observations on Volume Changes of Ground Guayule Shrub Stored Under Liquids

| Liquid: | Water Volume*, cc | | | Acetone Volume*, cc | | | Hexane Volume*, cc | | |
|---|---|---|---|---|---|---|---|---|---|
| Storage | Total | Shrub On | | Total | Shrub On | | Total | Shrub On | |
| Time | Sample | Top | Bottom | Sample | Top | Bottom | Sample | Top | Bottom |
| Original (0) | 800 | 100 | 100 | 1600 | 0 | 700 | 1600 | 0 | 700 |
| One Day | 800 | 300 | 0 | 1600 | 0 | 700 | 1575 | 0 | 675 |
| One Week | 800 | 25# | 250 | 1575 | 0 | 700 | 1550 | 0 | 675 |
| Two Weeks | 800 | 25# | 250 | 1550 | 0 | 675 | 1550 | 0 | 675 |
| One Month | 800 | 25# | 250 | 1550 | 0 | 675 | 1525 | 0 | 675 |
| 2.5 Months | 800 | 25# | 250 | 1525 | 0 | 675 | 1525 | 0 | 675 |

*Approximate volume, cc.
White microfloral growth observed on top and offensive odor.

TABLE III

Molecular Weight of Guayule Rubber Recovered From Ground Shrub Stored With and Without Stabilizer

| Shrub Stored Under: | Acetone | | Hexane | |
|---|---|---|---|---|
| Stabilizer[1] | None | Yes | None | Yes |
| Observation After 27 Days | | | | |
| Odor[2] | None | None | None | None |
| Microfloral Growth | None | None | None | None |
| Molecular Weight of Recovered Rubber | | | | |
| $Mw \times 10^3$ | 41 | 468 | 559 | 540 |
| $Mn \times 10^3$ | 150 | 357 | 509 | 502 |
| Mw/Mn | 2.7 | 1.3 | 1.1 | 1.1 |
| Rubber Recovered From Freshly Ground Shrub | $Mw \times 10^{-3} = 545$ | | | |
| | $Mn \times 10^{-3} = 460$ | | | |
| | $Mw/Mn = 1.2$ | | | |

[1]Commercial para-phenylenediamine
[2]Odor or solvent only

TABLE IV

Rate of Extraction of Guayule Resin and Guayule Resin/Rubber During Ambient Temperature Storage of Ground Shrub

| Shrub Stored Under | Acetone | Hexane |
|---|---|---|
| Product Extracted | Resin | Resin/Rubber |
| Calculated % Product Extracted After Days Storage | | |
| 1 | 80 | 73 |
| 10 | 96 | 76 |
| 31 | 100 | 80 |
| 40 | 99 | 82 |
| 43 | 98 | 78 |
| Molecular Weight of Recovered Rubber | | |
| $Mw \times 10^{-3}$ | 406 | 430 |
| $Mn \times 10^{-3}$ | 172 | 177 |
| Mw/Mn | 2.4 | 2.4 |

TABLE V

The Effects of Agitation and Shrub Particle Size on Product Extraction Efficiencies During Ambient Temperature Storage

| Shrub Stored Under Agitation | Acetone | | | Hexane | | |
|---|---|---|---|---|---|---|
| Product Extracted | None | Mild[1] | | None | Mild[1] | |
| Nominal Shrub | Resin | | | Resin/Rubber | | |
| Size, Inches | ⅛ | ⅜ | Flaked[2] | ⅛ | ⅜ | Flaked[2] |
| Time/Minutes | | | | | | |
| 30 | 62 | 81 | 101 | 9 | 69 | 98 |
| 60 | 66 | 83 | 105 | 10 | 72 | 95 |
| 90 | 62 | 88 | 103 | 13 | 74 | 93 |
| Time/Days | | | | | | |
| 1 | — | — | — | 81 | 79 | 98 |
| 2 | — | — | — | 83 | 81 | 99 |
| 3 | — | — | — | 82 | 82 | 100 |

[1]Sample container gently rotated to mix the sample
[2]Guayule shrub milled at 0.002 inch clearance to flake the shrub (rupture cells containing rubber)

What is claimed is:

1. A method of storing guayule and guayule-like plant material prior to processing which comprises mixing the material in communited form with at least one essentially water-free organic liquid selected from the group consisting of butanes, pentanes, hexanes, heptanes, octanes, nonanes, cyclopentane, cyclohexane, cycloheptane, benzene, toluene, xylenes and mixtures thereof, to form a slurry in which the material is protected from contact with oxygen and storing said slurry for at least about 24 hours, and wherein the slurry also contains at least one stabilizer against oxidation of guayule resin and/or rubber, said stabilizer being soluble in said organic liquid and a symmetrical or unsymmetrical para phenylene diamine of the general formula

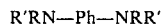

R'RN—Ph—NRR' wherein Ph is a phenylene group, each R is independently hydrogen or a hydrocarbyl group and each R' is independently a hydrocarbyl group.

2. A method as claimed in claim 1 wherein the solvent is butanes, pentanes, hexanes, heptanes, octanes, nonanes or a mixture thereof.

3. A method as claimed in claim 1 wherein the stabilizer is N,N' bis(phenyl)-p-phenylene diamine.

4. A method as claimed in claim 3 wherein the hydrocarbon solvent is pentanes, hexanes, heptanes, octanes or mixtures thereof.

UNITED STATES PATENT AND TRADEMARK OFFICE
CERTIFICATE OF CORRECTION

PATENT NO. : 4,530,995

DATED : July 23, 1985

INVENTOR(S) : GUTIERREZ ET AL.

It is certified that error appears in the above-identified patent and that said Letters Patent are hereby corrected as shown below:

TABLE III - Column 11, line 40

"41" should be -- 412 --

Signed and Sealed this

Thirty-first Day of December 1985

[SEAL]

Attest:

Attesting Officer

DONALD J. QUIGG

Commissioner of Patents and Trademarks